(12) United States Patent  
Mirizzi

(10) Patent No.: US 9,878,134 B2
(45) Date of Patent: Jan. 30, 2018

(54) MULTIPLE CHAMBER, EXPANDABLE THERAPEUTIC AGENT DELIVERY DEVICE

(71) Applicant: Michael S Mirizzi, San Jose, CA (US)

(72) Inventor: Michael S Mirizzi, San Jose, CA (US)

( * ) Notice: Subject to any disclaimer, the term of this patent is extended or adjusted under 35 U.S.C. 154(b) by 470 days.

(21) Appl. No.: 14/555,819

(22) Filed: Nov. 28, 2014

(65) Prior Publication Data

US 2015/0165169 A1 Jun. 18, 2015

Related U.S. Application Data

(60) Provisional application No. 61/915,134, filed on Dec. 12, 2013.

(51) Int. Cl.
*A61M 25/10* (2013.01)

(52) U.S. Cl.
CPC ..... *A61M 25/1002* (2013.01); *A61M 25/1029* (2013.01); *A61M 2025/105* (2013.01); *A61M 2025/1072* (2013.01); *A61M 2025/1075* (2013.01); *A61M 2025/1086* (2013.01)

(58) Field of Classification Search
CPC .......... A61M 25/1002; A61M 25/1029; A61M 2025/105; A61M 2025/1075; A61M 2025/1086; A61M 2025/1072; A61M 25/1011; A61M 2025/1013; A61M 2025/1015; A61M 2025/1004; A61M 25/1027

See application file for complete search history.

(56) References Cited

U.S. PATENT DOCUMENTS

| | | |
|---|---|---|
| 4,581,017 A | 4/1986 | Sahota |
| 4,636,195 A | 1/1987 | Wolinsky |
| 4,693,243 A | 9/1987 | Buras |
| 4,994,033 A | 2/1991 | Shockey |
| 5,049,132 A | 9/1991 | Shaffer |
| 5,213,576 A | 5/1993 | Abiuso |
| 5,254,089 A | 10/1993 | Wang |
| 5,295,962 A | 3/1994 | Crocker |
| 5,658,311 A | 8/1997 | Baden |
| 5,860,954 A | 1/1999 | Ropiak |
| 6,126,634 A | 10/2000 | Bagaoisan |
| 6,544,221 B1 | 4/2003 | Kokish |
| 7,056,274 B2 | 6/2006 | Apple |
| 7,077,836 B2 | 7/2006 | Lary |
| 7,985,200 B2 | 7/2011 | Lary |

(Continued)

FOREIGN PATENT DOCUMENTS

EP 0266957 B1 5/1988

*Primary Examiner* — Bhisma Mehta
*Assistant Examiner* — Hamza Darb
(74) *Attorney, Agent, or Firm* — Bay State IP, LLC

(57) ABSTRACT

A device having multiple chambers may be configured to expand to contact a substantial section of an interior wall of a body structure or lumen in order to simultaneously exclude blood or other liquid from a target structure while providing for delivery of a therapeutic agent directly to the interior wall. The expandable device may be manufactured from a plurality of flat sheets of material heat sealed to one another to form an inflation chamber and one, two or more delivery chambers. The sheets may also be bonded to an elongate catheter body having inflation and delivery lumens. The excluding of blood flow and delivery of therapeutic agents are completed by the same device.

34 Claims, 10 Drawing Sheets

(56) References Cited

U.S. PATENT DOCUMENTS

| | | |
|---|---|---|
| 8,034,022 B2 | 10/2011 | Boatman |
| 8,182,446 B2 | 5/2012 | Schaeffer |
| 8,317,747 B2 | 11/2012 | Kusleika |
| 2006/0095015 A1 | 5/2006 | Hobbs |
| 2010/0069881 A1 | 3/2010 | Salerno |
| 2012/0259315 A1 | 10/2012 | Hattangadi |
| 2013/0030410 A1 | 1/2013 | Drasler |
| 2013/0190796 A1* | 7/2013 | Tilson .................. A61F 2/2433 606/192 |

* cited by examiner

MULTIPLE CHAMBER, EXPANDABLE THERAPEUTIC AGENT DELIVERY DEVICE

CROSS-REFERENCE TO RELATED APPLICATION

This application claims the benefit of and takes priority from U.S. App. No. 61/915,134 filed on Dec. 12, 2013, the contents of which are hereby incorporated by reference.

FIELD OF THE INVENTION

This invention generally relates to therapeutic agent delivery devices, and more particularly to devices for targeted delivery of therapeutic agents to an internal surface of a body lumen or cavity.

BACKGROUND OF THE INVENTION

Several minimally-invasive medical interventional procedures make use of inflatable balloon structures to apply treatments to targeted areas within a body lumen. Such balloons are typically formed by bonding an extruded tubular material to an inflation or delivery lumen. Examples of procedures that may use such balloons include treatment of atherosclerotic plaque in the arterial vasculature, and delivery of therapeutic agents, such as sclerosants, into blood vessels for treatment of venous reflux or other conditions.

Some such devices include drug eluting balloons which may include a dissolvable therapeutic agent coated onto an outer surface of an expandable balloon. Such coatings may require a chemical, mechanical, thermal or other release mechanism to limit loss of the therapeutic agent during positioning of the balloon at a target site.

Other drug delivery catheters may be configured to inject an active agent into a blood vessel. In some cases, one or more expandable balloons may be placed proximally and/or distally from an injection point in order to retain the injected active agent in a targeted region of the vessel. Both the drug eluting balloon and the direct injection devices have drawbacks.

Few devices and method have been developed for improving the administration of liquid medical substances, such as sclerosing agents, into the veins or other body lumens. Thus, improved methods and devices for treating the vascular system and other body lumens are desired.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE SEVERAL EMBODIMENTS

In various embodiments, systems and methods are provided herein for treating blood vessels, bodily lumens, body cavities, or other structures by direct application of a therapeutic agent to an interior wall of such structures. In some embodiments, such therapeutic agent delivery may be performed with a therapeutic agent delivery device having multiple chambers. Embodiments of such devices may employ very simple construction while providing substantial flexibility and diversity in performing clinical procedures. Various embodiments and examples of such devices are shown and described with reference to the accompanying drawings and figures. References made to particular examples and implementations are for illustrative purposes, and are not intended to limit the scope of the invention or the claims.

Some embodiments provide a multi-chamber therapeutic agent delivery device that is capable of simultaneously excluding blood from the target vessel and delivering an effective quantity of a therapeutic agent directly to the interior wall of a body structure. By delivering a therapeutic agent directly to the structure wall to be treated, a smaller volume of the therapeutic agent may be delivered into the body cavity or lumen, thereby improving safety and potentially expanding the scope of treatments that may be offered. For example, such devices may allow for treatments in multiple body regions (e.g., both legs) before reaching a maximum allowable dosage of the therapeutic agents(s). Providing such a device at a low cost may also make such procedures available to a wider range of patients.

In some embodiments, a multi-chamber therapeutic agent delivery device may include features that enhance the echogenic properties of portions of the device in order to enhance visibility of the device under ultrasound imaging. Such echogenic features may include textures, structures (e.g., seams) and/or materials selected for echogenic properties in addition to other desired properties.

In some embodiments, at least portions of the device may be made of a compliant material, thereby allowing the device to conform to body structures of irregular internal shapes and sizes while maintaining continuous contact with the vessel wall.

Multiple Chamber Expandable Therapeutic Agent Delivery Devices

Various example embodiments are provided herein for a device that may be configured to expand to contact a substantial section of an interior wall of a body structure or lumen in order to simultaneously exclude blood or other liquid from a target structure while providing for delivery of a therapeutic agent directly to the interior wall.

Figure 1A:
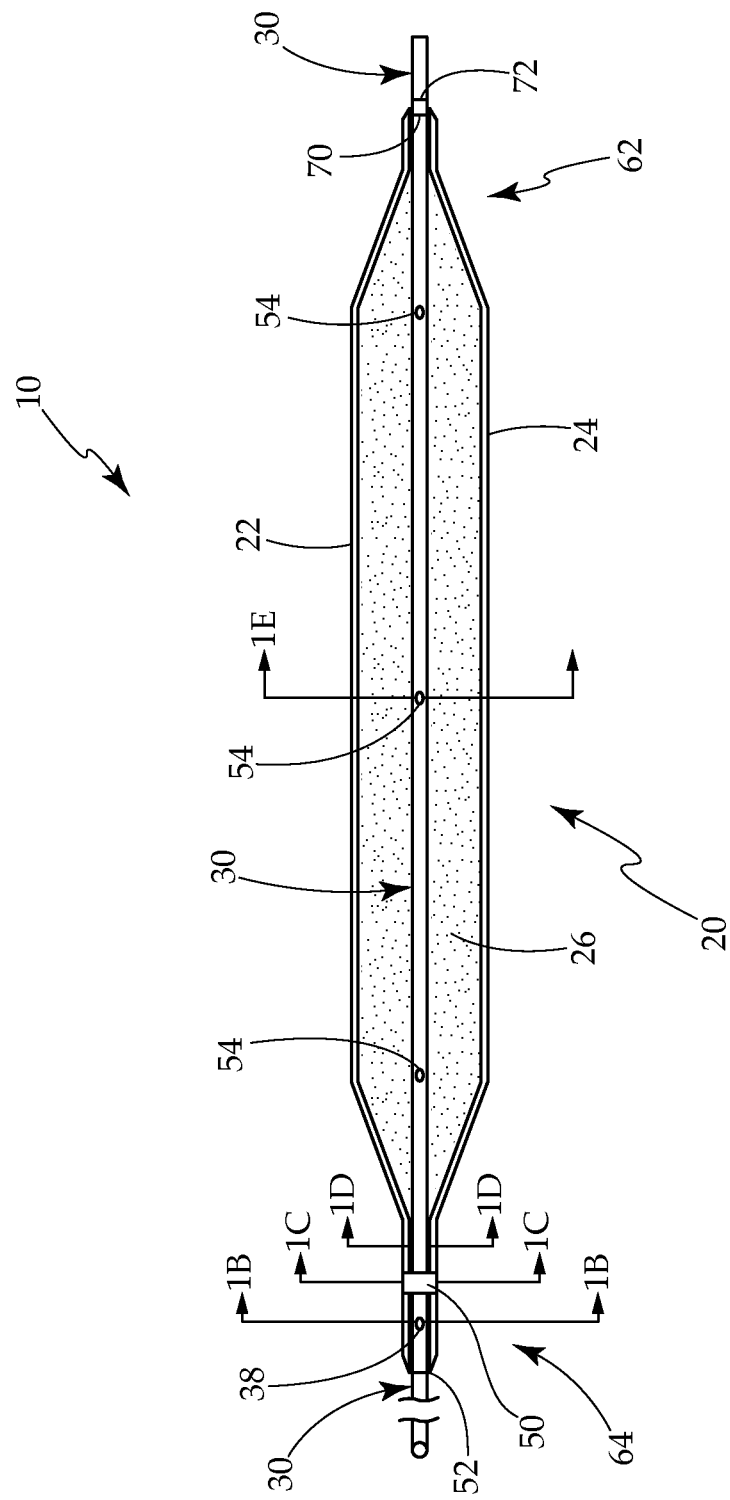
FIG. 1A is a diagram showing a semi-transparent plan view of an example of an expandable multiple chamber therapeutic agent delivery device.

FIG. 1A illustrates an example of a device 10 that may be used to deliver therapeutic agents to a body lumen. The device 10 shown in FIG. 1A may generally include an expandable section 20 that may include first and second side seams 22, 24 along each long edge of the expandable section 20. The expandable section 20 may also include an inflation chamber 26 and one or more therapeutic delivery chambers 28 as shown in FIG. 1B.

Figure 1B:
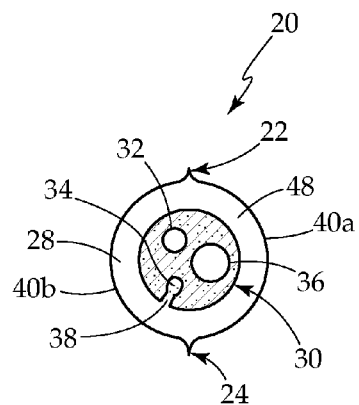
FIG. 1B is a diagram illustrating a cross-section of the device of FIG. 1A taken through line through line 1B.

With reference to the cross-sectional view of FIG. 1B, the expandable section 20 may be attached to an elongated catheter body 30 that may include multiple lumens extending therethrough. In the example of FIG. 1B, the catheter body 30 may include an inflation lumen 32, a therapeutic agent delivery lumen 34 (which may be referred to herein simply as a "delivery lumen" 34), and optionally a guidewire lumen 36.

Figure 2:
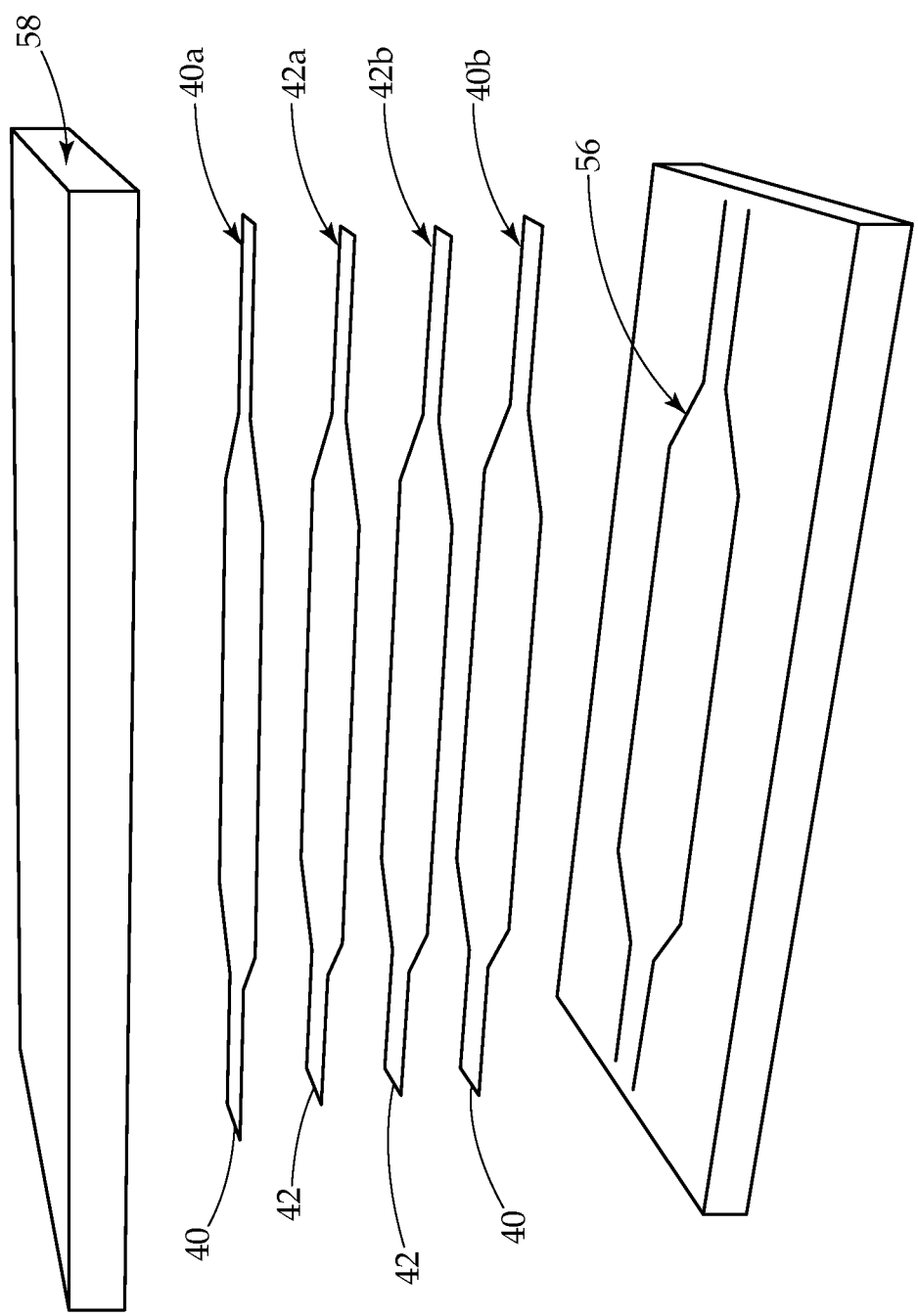
FIG. 2 is a perspective view diagram showing an example of a sealing apparatus and a plurality of planar sheets to be sealed to one another to form an expandable multiple chamber device.

As FIG. 2 illustrates, some embodiments of an the expandable section 20 may be made from a plurality of flat sheets 40, 42 of material heat sealed to one another to form the inflation chamber 26 and the delivery chambers 28. In various embodiments, a pair of inner sheets 42a, 42b may be sized and shaped so as to form the inflation chamber 26 when the inner sheets 42a, 42b are sealed to one another. A pair of outer sheets 40a, 40b may form one or more delivery chambers 28 when the outer sheets 40a, 40b are sealed to one another.

Figure 1C:
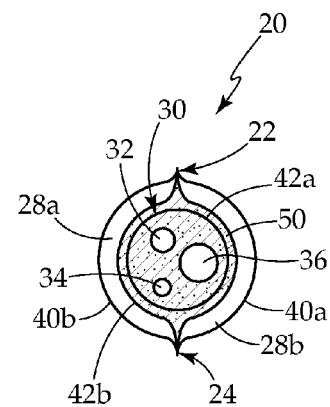
FIG. 1C is a diagram illustrating a cross-section of the device of FIG. 1A taken through line through line 1C.
Figure 1D:
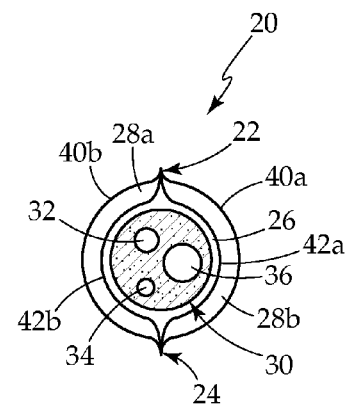
FIG. 1D is a diagram illustrating a cross-section of the device of FIG. 1A taken through line through line 1D.
Figure 1E:
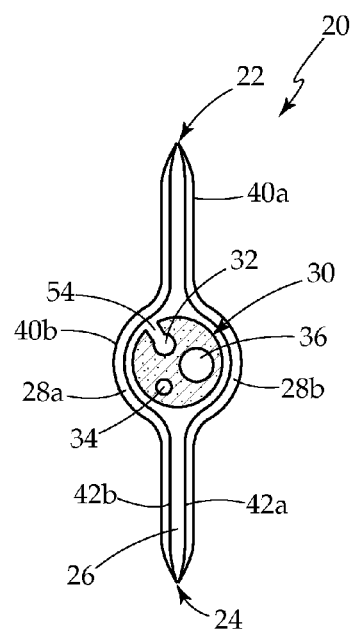
FIG. 1E is a diagram illustrating a cross-section of the device of FIG. 1A taken through line through line 1E.
Figure 1F:
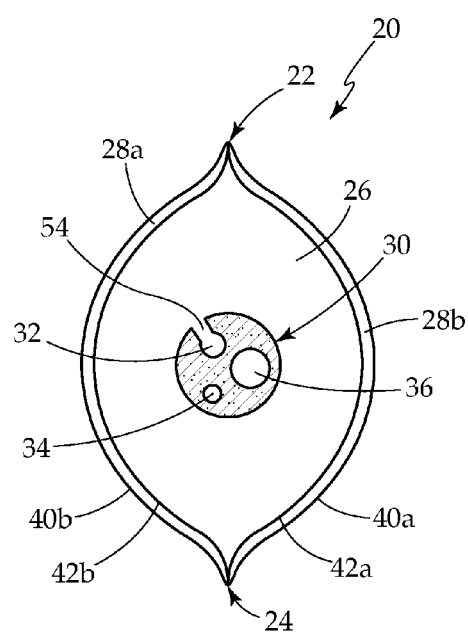
FIG. 1F is a diagram illustrating a cross-section of the device of FIG. 1A taken through line through line 1F in a partially inflated condition.

FIG. 1B-FIG. 1F illustrate example cross-sectional views of the device of FIG. 1 through the cross-sections indicated at lines 1B-1E, respectively (FIG. 1E and FIG. 1F are both taken through the same cross-section line at 1E). FIG. 1B shows a proximal region of an expandable section 20 mounted to a catheter body 30 that includes a therapeutic agent delivery lumen 34, a guidewire lumen 36 and an inflation lumen 32. The section of FIG. 1B cuts though an opening 38 in a therapeutic agent delivery lumen 34 into a channel 48 in communication with one or both therapeutic agent delivery chambers 28. The section of FIG. 1B also cuts through a region proximal to a proximal end of the inner sheets 42. As a result, only the outer sheets 40a, 40b are visible in FIG. 1B. The outer sheets 40a, 40b are shown joined to one another at seams 22, 24.

FIG. 1C cuts through a region at which the inner sheets 42a, 42b are sealed to the catheter body 30. The inner sheets 42a, 42b may be sealed to the catheter body 30 with a complete annular seal so as to prevent fluid communication between the therapeutic agent delivery chambers 28 and the inflation chamber 26.

FIG. 1D is a cross-section at a region distal to an inner-sheet proximal seal 50 and to an outer-sheet proximal seal 52, showing both the therapeutic agent delivery chambers 28a, 28b and a narrow portion of the inflation chamber 26. Both the inner sheets 42a, 42b and the outer sheets 40a, 40b are shown joined to one another at first and second seams 22, 24.

FIG. 1E shows a cross-section of the expandable member in a deflated state. The cross-section of FIG. 1E also cuts through an opening 54 in the inflation lumen 32 through which an inflation medium (such as a saline solution) may flow in order to inflate the inflation chamber 26, thereby expanding the inner sheets 42a, 42b and the outer sheets 40a, 40b to an expanded configuration. FIG. 1F shows a partially-expanded configuration of the expandable section 20. In a fully-expanded configuration, the walls may form a substantially more circular cross-section.

In some embodiments, a guidewire lumen 36 may be sized and configured to receive a guidewire of a size and construction selected for a chosen therapeutic application. In various embodiments the catheter body 30 may be configured to be positioned over a guidewire in either an over-the-wire arrangement or in a rapid-exchange arrangement as those terms are generally understood by those skilled in the art.

In some embodiments, the catheter body 30 may also include a one or more additional lumens for performing additional tasks such as inserting tools, aspirating blood or residual therapeutic agent, etc.

With reference to FIG. 2, in some embodiments, if the outer sheets 40a, 40b are sealed to the inner sheets 42a, 42b, then two independent delivery chambers 28a, 28b may be formed within the spaces between the inner sheets 42a, 42b and the outer sheets 40a, 40b. The two delivery chambers 28a, 28b may be sealed to the catheter body 30 such that they may both be in fluid communication with a single delivery lumen 34 of the catheter body 30. Alternatively, the two delivery chambers 28a, 28b may be sealed to the catheter body 30 such that each delivery chamber 28a, 28b is in communication with a separate delivery lumen 34 of the catheter body 30. In other embodiments, two or more delivery lumens may be joined in fluid communication with either one or both delivery chambers.

In some embodiments, all four sheets 40a, 40b, 42a, 42b may be sealed to one another simultaneously, thereby forming two side seams 22, 24 each of which may incorporate all four sheets 40a, 40b, 42a, 42b (Examples of such structures are shown in the cross-sectional views of FIG. 1B-FIG. 1F).

In some cases, the sheets 40a, 40b, 42a, 42b may be cut to desired sizes and shapes before a sealing process. The sheets 40a, 40b, 42a, 42b may then be aligned with one another and stacked together. The sheets 40a, 40b, 42a, 42b may then be compressed between a base plate 57 carrying a heating element 56 and an anvil 58 so as to melt portions of the sheets 40a, 40b, 42a, 42b together to form seams.

For example, a heating element 56 may include an electrical resistance heater which may be covered by a material with high temperature resistance and low reactivity with the sheet materials to be sealed. For example, a heating element 56 may be covered by a layer of TEFLON tape (not shown). In various embodiments, the sheets 40a, 40b, 42a, 42b may be cut to desired sizes and shapes during a sealing process. For example, in some embodiments the heating element 56 and/or the anvil may incorporate a cutting die (not shown) configured to cut the sheets to a desired external shape simultaneously with a sealing step as the heating element base plate 57 and the anvil 58 are brought together and compressed. Alternatively, the sheets 40a, 40b, 42a, 42b may be cut to a desired shape after a sealing step.

In alternative embodiments, two or more sheets may be sealed together using other methods such as solvent welding which may include applying a solvent to desired seam regions of one or more sheets and compressing the sheets with a sufficient pressure and for sufficient time to allow the seam regions of the sheets to become incorporated into a seam. Alternatively, two or more sheets may be sealed to one another using other methods such as ultrasonic welding, adhesives, or various combinations of any these techniques or others.

Figure 2A:
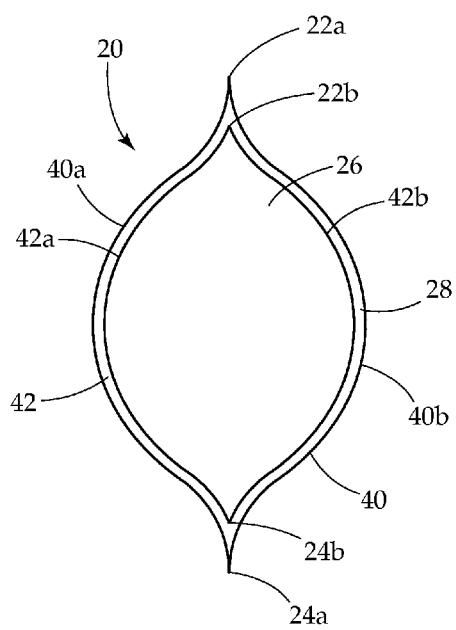
FIG. 2A is a diagram showing an alternative cross-section of the device of FIG. 1A through line 1F in a partially inflated condition.

Alternatively, as shown for example in FIG. 2A, a single annular delivery chamber may be formed by sealing the outer sheets 40a, 40b to one another without sealing both outer sheets 40a, 40b to either of the inner sheets 42a, 42b. First and second outer seals 22a, 24a may join the outer sheets 40a, 40b to form an outer chamber wall 40 that is substantially free from the inner chamber wall 42 formed by joining inner sheets 42a, 42b with separate inner seals 22b, 24b. Both the outer wall 40 and the inner wall 42 may be joined to the catheter body 30.

Figure 2B:
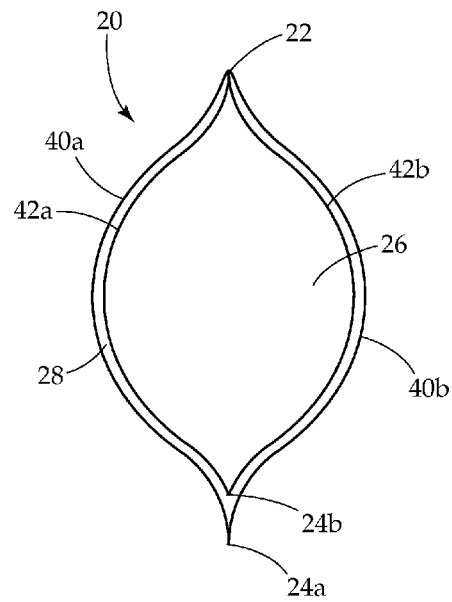
FIG. 2B is a diagram showing an alternative cross-section of the device of FIG. 1A through line 1F in a partially inflated condition.

As shown in the example of FIG. 2B, a single annular delivery chamber 28 may also be formed by sealing the outer sheets 40a, 40b to one or both of the inner sheets 42a, 42b at only a single seam 22 of the outer sheets 40a, 40b.

Figure 2C:
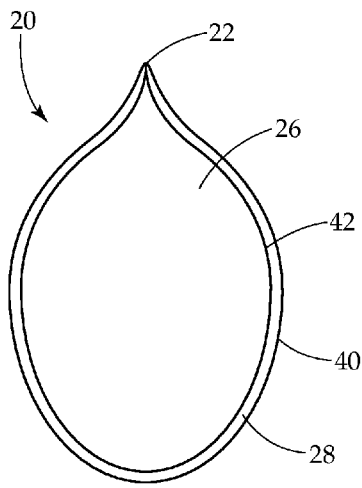
FIG. 2C is a diagram showing an alternative cross-section of the device of FIG. 1A through line 1F in a partially inflated condition.
Figure 2D:
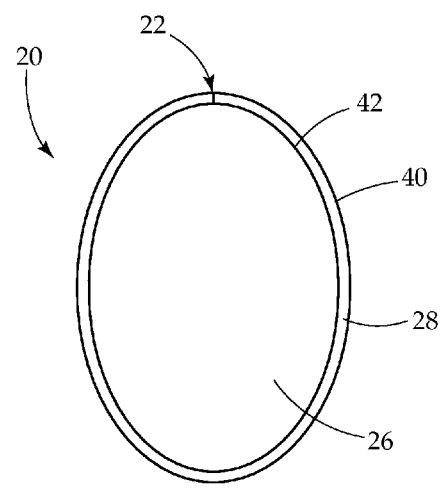
FIG. 2D is a diagram showing an alternative cross-section of the device of FIG. 1A through line 1F in a partially inflated condition.

In an alternative configuration, as shown for example in FIGS. 2C and 2D, a single inner sheet 42 and a single outer sheet 40 may be folded and sealed at a single seam 22 to form a single inflation chamber 26 and a single delivery chamber 28.

In any of the various embodiments, seams 22, 24 may be arranged such that they extend outwards from the expandable section 20 (e.g., as shown in FIG. 1B-FIG. 1F and FIG. 2A-FIG. 2C), or seams may be formed by overlapping edges of a sheet so as to form a seam that does not extend from the expandable section as shown in FIG. 2D.

In some embodiments, in order to form a single delivery chamber or communicating delivery chambers such as those shown in the examples of FIG. 2A and FIG. 2B, the inner sheets 42a, 42b may be sealed to one another in a first sealing step. Then the outer sheets 40a, 40b may be positioned above and below the sealed inner sheets 42a, 42b, and the outer sheets 40a, 40b may be sealed in a second sealing step. During the second sealing step, depending on the size and position of the outer sheets 40a, 40b relative to the inner sheets 42a, 42b, the outer seams may incorporate portions of the inner-sheet seams as described in various examples above.

In some embodiments, after sealing the inner sheets 42a, 42b at inner seams 22b, 24b, portions of the inner-sheet seams 22b, 24b may be notched or cut out without cutting into the inflation chamber 26. The remaining portions of the inner seams 22b, 24b may then be sealed to the outer seams 22a, 24a. The notched sections may then provide passages allowing fluid communication between the first delivery chamber 28a and the second delivery chamber 28b.

Figure 3A:
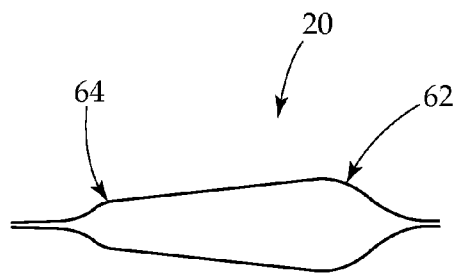
FIG. 3A is a diagram illustrating an example of an asymmetrical expandable device.
Figure 3B:
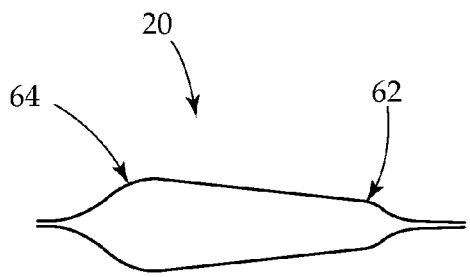
FIG. 3B is a diagram illustrating an example of an asymmetrical expandable device.

In various embodiments, the expandable section 20 may be configured with an irregular and/or asymmetrical shape along its length. Some examples of such irregular or asymmetrical shapes are shown in FIG. 3A-FIG. 3E. For example, as shown in FIG. 3A, the expandable section 20 may be configured with a tapered shape such that such that a distal portion 62 of the expandable section has a larger diameter than a proximal portion 64. Alternatively, as shown in FIG. 3B, the expandable section 20 may be configured with a tapered shape such that a proximal portion 64 of the expandable section has a larger diameter than a distal portion 62.

Figure 3C:
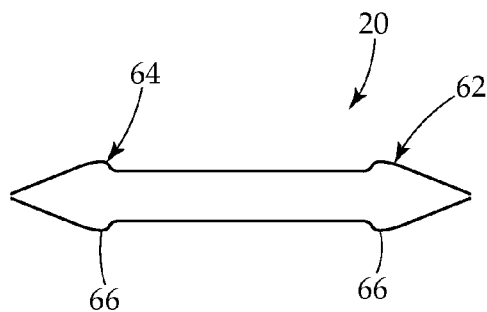
FIG. 3C is a diagram illustrating an example of an asymmetrical expandable device.
Figure 3D:
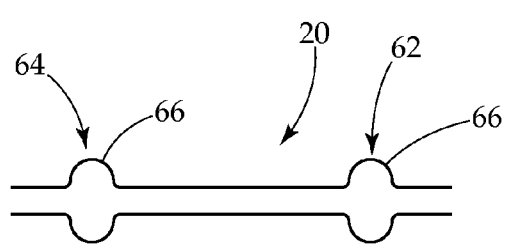
FIG. 3D is a diagram illustrating an example of an asymmetrical expandable device.
Figure 3E:
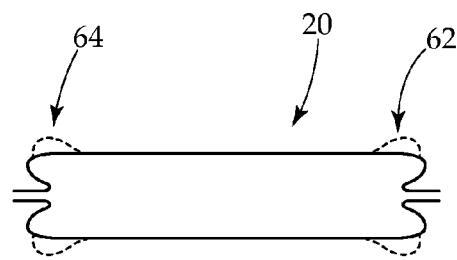
FIG. 3E is a diagram illustrating an example of an asymmetrical expandable device.

In some embodiments, the inner and/or outer sheets 40a, 40b may be shaped to include a shoulder at a distal 62 and/or proximal end 64 of the expansion section 20 to trap liquid therapeutic agent within a target treatment area adjacent to the expansion section. For example, FIG. 3C-FIG. 3E illustrate some examples of inflated expansion section shapes that may be used to retain a therapeutic agent in a target region. In some embodiments, shoulders or other structures configured to retain therapeutic agent within a desired region may be formed after assembly of the expandable section such as by heat-forming, blow-molding, or other processes.

In some embodiments, some or all of the sheets 40a, 40b, 42a, 42b used to form the expandable section 20 may comprise flexible, compliant, biocompatible materials. Making the expandable section 20 from compliant (i.e., stretchable) materials allows the expandable section 20 to conform to variably-shaped anatomical structures within body lumens to be treated as described in some examples below.

In some embodiments, all four sheets may be made from the same material. Alternatively, some or all of the sheets may be different materials. If the inner sheets 42a, 42b are made of a different material than the outer sheets 40a, 40b, the two materials may advantageously be selected to have substantially similar or compatible mechanical properties such as tensile strength, tensile elongation, and tensile modulus of elasticity, tear strength hardness, vicat softening point, etc. For example, the outer sheets 40 defining delivery chambers 28a, 28b may be selected to exert no more resistance to expansion than the inner sheets 40a, 40b defining the inflation chamber 26.

In some embodiments, the inner sheets 42a, 42b may be made of any suitable compliant biocompatible material that is substantially impermeable to a saline solution or other inflation fluid. For example, the inner sheets 42a, 42b may be made of a biocompatible thermoplastic polyurethane material such as CHRONOPRENE, CARBOTHANE, PELLETHANE or others. Alternatively, the inner sheets 42a, 42b may be made of a different impermeable, biocompatible, elastic, compliant material. For example, other polyurethane materials, or other thermoplastic polymers or thermoplastic elastomers (TPEs) may be selected for desirable properties such as high compliance/elasticity, heat sealability, etc. Thermoplastic elastomers sometimes referred to as thermoplastic rubbers, are a class of copolymers or a physical mix of polymers (usually a plastic and a rubber) which consist of materials with both thermoplastic and elastomeric properties. While most elastomers are thermosets, thermoplastics are in contrast relatively easy to use in manufacturing, for example, by injection molding. Thermoplastic elastomers show advantages typical of both rubbery materials and plastic materials.

The principal difference between thermoset elastomers and thermoplastic elastomers is the type of crosslinking bond in their structures. Examples of potentially suitable thermoplastic elastomer materials may include Styrenic block copolymers (TPE-s), Polyolefin blends (TPE-o), Elastomeric alloys (TPE-v or TPV), Thermoplastic polyurethanes (TPU), Thermoplastic copolyester, and Thermoplastic polyamides. Examples of thermoplastic elastomer products that come from block copolymers group are Arnitel (DSM), Solprene (Dynasol), Engage (Dow Chemical), Hytrel (Du Pont), Dryflex and Mediprene (ELASTO), Kraton (Kraton Polymers), Pibiflex (SO.F.TER.).

In other embodiments, the inner sheets may be made of a material that is at least slightly water-permeable. In some embodiments, the inner sheets 42a, 42b and/or the outer sheets 40a, 40b may comprise polyurethane sheets with a thickness of about 0.0005" to about 0.005", or from about 0.001" to about 0.002".

In general, the outer sheets 40a, 40b may be made from one or more materials that will allow the delivery chambers 28a, 28b to stretch when expanded by the inflation chamber 26 while also allowing a liquid therapeutic agent to pass through the outer sheets 40a, 40b forming outer walls of a delivery chamber 28 under a delivery pressure. Thus, in some embodiments, the outer sheets 40a, 40b may be made of a normally impermeable material that may be made permeable by creating holes or other apertures piercing the material. Alternatively, the outer sheets 40a, 40b may be made of a porous material such as a woven material or a microporous membrane. For example, suitable porous materials may include ePTFE, PET (e.g., Dacron), Nylon, as well as ebeam bombarded polyurethane which may exhibit microporous properties, and laser drilled or punched materials.

A multitude of other materials may be used for either the inner sheets 42a, 42b and/or the outer sheets 40a, 40b, including all of the previously mentioned materials as well as electro-spun PTFE, laminates of electro-spun PTFE and polyurethane, and combinations of other materials as required for desired performance.

Forming an expandable section 20 by sealing multiple planar sheets together may produce a unique expandable device. For example, such a device may include features such as a pinched-oval or a pinched-circle shaped inflation chamber 26 when inflated. The device may also include a pair of delivery chambers 28a, 28b each of which may have a crescent shape when the inflation chamber 26 is inflated. Each of the delivery chambers 28a, 28b may have a plurality of delivery apertures which may be randomly distributed or patterned as described in various examples below.

In some embodiments, after the expandable section 20 is formed, the inner sheets and/or the outer sheets may be sealed to a catheter body 30. The inner sheets 42a, 42b and/or the outer sheets 40a, 40b of the expandable section may be sealed to the catheter body using any suitable technique, such as heat sealing, induction welding, solvent bonding, sonic welding, adhesive bonding or a combination of these or other techniques.

As shown in FIG. 1A-1F, the inner sheets 42a, 42b may be sealed to the catheter body at a proximal inner seal 50 and a distal inner seal 70. An inflation lumen 32 extending through the catheter body 30 may have one or more distal openings 54 which may be located between the proximal inner seal 50 and the distal inner seal 70. The number and size of the distal inflation lumen openings 54 may be selected to provide a sufficient inflation flow rate and pressure.

As shown in FIG. 1A, in some embodiments the outer sheets 40a, 40b may be sealed to the catheter body 30 at a proximal outer seal 52 that encloses one or more openings 38 from a therapeutic agent delivery lumen 34 extending through the catheter body 30. In some embodiments, the proximal or distal outer seal may overlap the corresponding inner seal.

In some embodiments, an expandable section 20 may include delivery lumen openings 38 positioned only at a proximal end 64 of a delivery chamber 28 or adjacent a distal end 62 of a delivery chamber 28. Such a single opening may be arranged relative to the proximal outer seal 50 or the distal outer seal 70 so as to be in fluid communication with one or both of the delivery chambers 28.

Figure 4A:
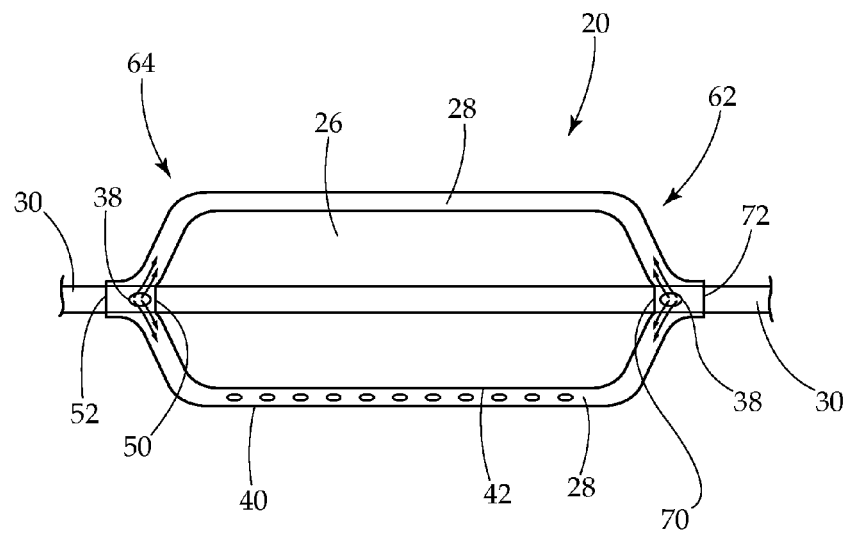
FIG. 4A is a longitudinal cross-sectional diagram illustrating an example of therapeutic agent fluid flows in an expandable multiple chamber device.

As shown for example in FIG. 4A, in some embodiments a catheter body 30 may comprise therapeutic agent delivery lumen openings 38 adjacent both proximal 64 and distal 62 ends of a delivery chamber 28. Such an arrangement may provide for improved distribution of a therapeutic agent along the length of a delivery chamber 28.

In some embodiments, a catheter body may include two therapeutic agent delivery lumens 34, each having at least one opening in fluid communication with one or both of the delivery chambers 28. For example, in some embodiments, a first therapeutic agent delivery lumen 34 may be in communication with only a first delivery chamber 28a, and a second therapeutic agent delivery lumen (not shown) may be in communication with only a second delivery chamber 28b. Using such a system, two or more therapeutic agents may be delivered independently, interacting with one another only within the body lumen after exiting the outer wall 42 of the respective delivery chambers 28a, 28b.

Alternatively, one or both of two delivery lumens 34 may be in communication with both of the delivery chambers 28a, 28b. Using such a system, two or more therapeutic agents may be mixed in a delivery chamber and simultaneously delivered into the body lumen through the outer walls 40a, 40b of the delivery chambers 28a, 28b. Alternatively, such an arrangement may allow two different agents to be delivered successively to the body lumen through the delivery chambers 28a, 28b.

In some embodiments, the outer sheets 40a, 40b may be longer along the longitudinal axis of the expansion section than the inner sheets. This may allow the outer sheets 40a, 40*b* to be sealed to the catheter body 30 at a point 52 or 72 that is separated from an inner-sheet seal 50 or 70, respectively. In this way, a delivery lumen opening 38 may be enclosed within the outer sheet(s) 40 while excluding fluid communication between the delivery chamber 28 and the inflation chamber 26.

Figure 4B:
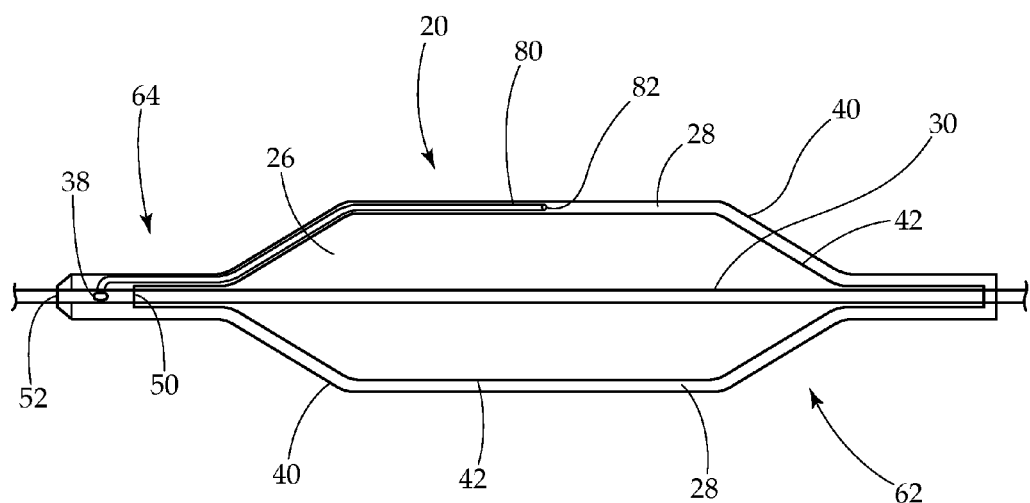
FIG. 4B is a longitudinal cross-sectional diagram illustrating another example of therapeutic agent fluid flows in an expandable multiple chamber device.

FIG. 4B illustrates an alternative embodiment in which a delivery lumen extension tube 80 extends from a delivery lumen opening 38 in the catheter body 30 into a delivery chamber 28. In some cases, a delivery lumen extension tube 80 may extend to about the middle of the delivery chamber 28. In other cases, a delivery lumen extension tube 80 may extend to a distal region 62 of the delivery chamber 28. The delivery lumen extension tube 80 may include a single distal opening 82, and/or may include a plurality of radial openings along its length. In some cases, a delivery lumen extension tube 80 may be provided to provide a desired distribution of a therapeutic agent along the length of the delivery chamber 28.

In some embodiments, textures or structures may be provided to prevent adhesion and/or to promote fluid flow through the delivery chambers 28 at an interface between an outer surface of the inner sheets and an inner surface of the outer sheets. For example, in some embodiments an internal surface of one or both of the outer sheets 40*a*, 40*b* may be textured so as to promote easy separation of the sheet sections defining the delivery chambers. Similarly, an external surface 42 of one or both of the inner sheets 42*a*, 42*b* may also be textured to promote easy separation of the sheet sections defining the delivery chambers. Any of the texture patterns described above or others may be used for such purposes. Such texturing may reduce a tendency of the two layers to stick to one another during expansion of the expandable section and during delivery of a therapeutic agent through the delivery chambers.

With reference to FIG. 5A-FIG. 5D, in some embodiments distribution of a therapeutic agent throughout a delivery chamber 28 may be improved by providing structures defining ribs and/or channels between the outer surface of an inflation chamber wall 42 and the inner surface of a delivery chamber wall 40.

Figures 5A, 5B:
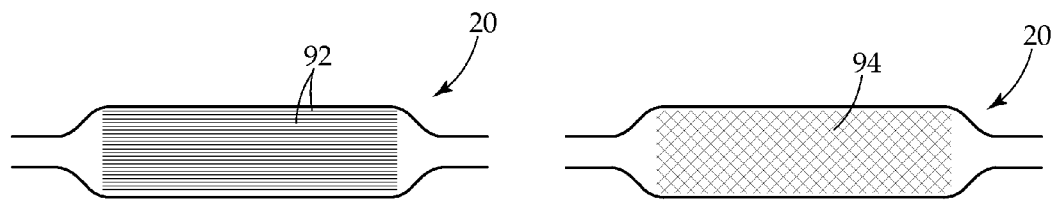
FIG. 5A is a diagram illustrating a texture that may be formed on one or more material sheets used to form an expandable multiple chamber device.
FIG. 5B is a diagram illustrating a texture that may be formed on one or more material sheets used to form an expandable multiple chamber device.
Figures 5C, 5D:
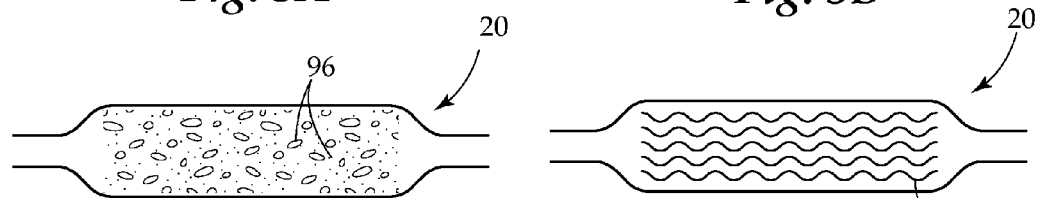
FIG. 5C is a diagram illustrating a texture that may be formed on one or more material sheets used to form an expandable multiple chamber device.
FIG. 5D is a diagram illustrating a texture that may be formed on one or more material sheets used to form an expandable multiple chamber device.
Figure 5E:
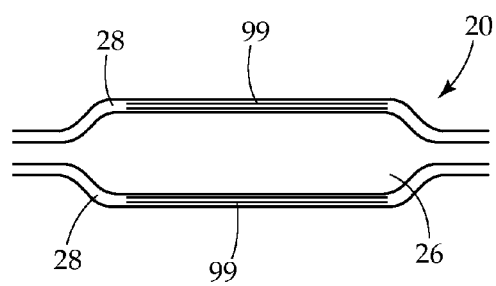
FIG. 5E is a longitudinal cross-sectional diagram illustrating flow promoting structures in a therapeutic agent delivery chamber in an expandable multiple chamber device.

Flow distribution structures may be extruded into the inner and/or outer sheets 40*a*, 40*b* used to form the expandable section 20. Alternatively, flow distribution structures may be formed into the sheets, such as by thermoforming folds into the sheets. Alternatively, as shown in FIG. 5E, flow distribution structures 99 may include additional materials such as rods, wires, tubes, beads, woven materials, textiles, strips, netting, or other shapes made of metal, plastic or other suitable material. In some embodiments, such structures may be bonded to one or more sheet sections forming a delivery chamber. Alternatively, flow distribution channels may be formed by spot sealing or tacking select portions of an inner sheet to portions of an outer sheet at various points across a surface of a delivery chamber. In some embodiments, such spot-sealed sections may be formed while the delivery chamber is inflated with an inflation fluid. Such flow distribution structures may be provided in any desired shape or configuration to achieve a desired flow profile within a delivery chamber 28.

Figure 5F:
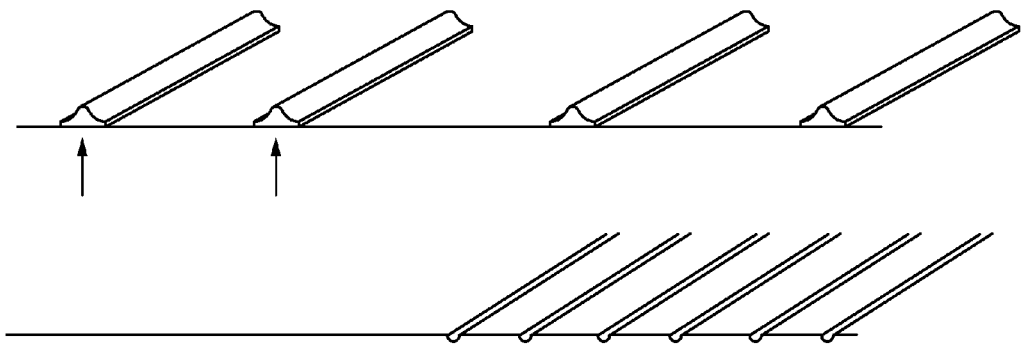
FIG. 5F is a close-up perspective view of an example of ribs that may be provided as flow promoting structures within a therapeutic agent delivery chamber.
Figure 6A:
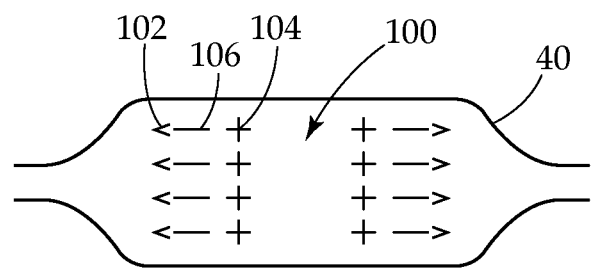
FIG. 6A is a schematic diagram illustrating examples of flow apertures that may be formed in outer sheets of a therapeutic agent delivery chamber.
Figure 6B:
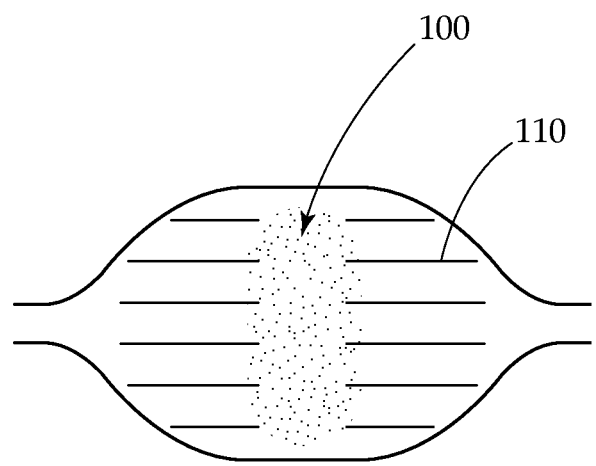
FIG. 6B is a schematic diagram illustrating examples of flow apertures that may be formed in outer sheets of a therapeutic agent delivery chamber.
Figure 6C:
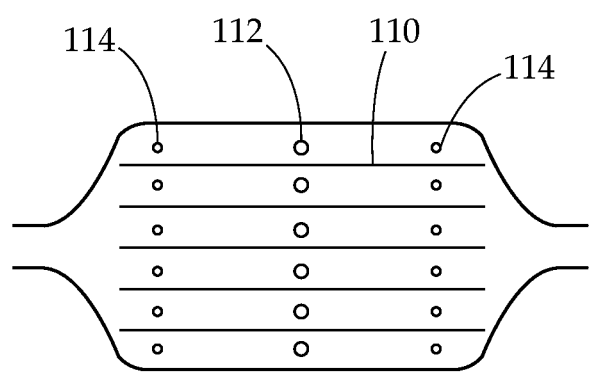
FIG. 6C is a schematic diagram illustrating examples of flow apertures that may be formed in outer sheets of a therapeutic agent delivery chamber.

For example, a textured outer surface of an inflation chamber and/or a textured inner surface of a delivery chamber may include capillary channels configured to draw a liquid therapeutic agent along the inner surface of the delivery chambers 28. Such textures may comprise any of a nearly infinite range of random or patterned arrangements of raised or depressed structures. FIG. 5A-FIG. 5D illustrate several examples of such texture arrangements. FIG. 5A shows a series of substantially longitudinal linear channels 92 on an outer surface of an inflation chamber or an inner surface of a delivery chamber. FIG. 5B shows a pattern of cross-hatched channels 94 on an outer surface of an inflation chamber or an inner surface of a delivery chamber. FIG. 5C shows a plurality of cellular structures 96 on an outer surface of an inflation chamber or an inner surface of a delivery chamber. FIG. 5D shows a pattern of wavy longitudinal channels 98 on an outer surface of an inflation chamber or an inner surface of a delivery chamber. Some examples of rib structure cross-sections are shown in the close-up cross-sectional diagram of FIG. 5F.

In some embodiments, a pattern of apertures 100 through a delivery chamber wall 40 may be selected to achieve a desired distribution of therapeutic agents exiting a delivery chamber 28. For example, in some cases, a delivery chamber 28 may have a uniform distribution of apertures along its surface. Such a substantially uniform distribution of apertures may comprise randomly positioned apertures or apertures positioned according to a pattern. In other embodiments, a delivery chamber 28 may include fewer and/or smaller apertures adjacent a therapeutic agent delivery lumen opening 38 and more and/or larger apertures as distance from a therapeutic agent delivery lumen opening 38 increases. FIG. 6A-FIG. 6C illustrate a few possible examples of aperture patterns, but a virtually infinite number of aperture configurations and individual aperture shapes are possible.

If an outer sheet 40 is made of an impermeable material, then delivery apertures may be formed in the outer sheet 40 by cutting or removing material. Apertures 100 may be formed in any shape or size sufficient to allow a desired rate of fluid therapeutic agent to be delivered therethrough. In some embodiments, apertures through the delivery chamber walls 40 may be shaped and/or sized to provide a one-way valve-like function. For example, apertures 100 may include slits in various shapes designed to create one or more flaps that may move or deflect when a therapeutic agent is delivered under a delivery pressure. As shown in FIG. 6A, examples of apertures 100 may include V-shapes 102, W-shapes, X-shapes, U-shapes, plus-sign-shapes 104, straight lines 106, etc.

FIG. 6B illustrates an example outer sheet 40 with a pattern of small, randomly positioned apertures 100, including ribs 110 for promoting distribution of an agent along the surface of the outer sheet 40 when delivered through the apertures 100. The pattern of FIG. 6B shows a higher density of apertures at a center region of the delivery chamber 28 and lower density aperture patterns adjacent proximal and distal ends of the delivery chamber 28.

FIG. 6C illustrates an example outer sheet 40 with a pattern of circular apertures 112, 114 in which larger-diameter apertures 112 are located towards a center region of the delivery chamber, and smaller-diameter apertures 114 are located adjacent proximal and distal ends of the delivery chamber.

In various embodiments, apertures 100 may be formed in an outer sheet 40 by any suitable method. Methods for forming openings in an outer sheet may include mechanical methods such as puncturing with a mechanical pin, puncturing with a punch of a desired size and shape, or slicing or scoring the sheet with a blade. In some embodiments, openings may be formed by application of focused energy such as lasers, heated blades or punches, or other methods.

In some embodiments, openings may be formed when the outer sheet is in a relaxed or un-stretched state. Alternatively, openings may be formed while the outer sheet material is stretched in one or more directions. For example, in some embodiments, openings may be formed while the outer sheet material is stretched in directions and to an extent that is similar to a stretching force that may be applied when the inflation chamber is inflated during a therapeutic agent delivery procedure.

In some embodiments, an external surface 40 of one or both of the outer sheets 40a, 40b may include a texture configured to distribute a delivered therapeutic agent across the outside of the delivery chambers 28. For example, a textured outer surface 40 may include capillary channels configured to draw a liquid therapeutic agent along the outer surface of the delivery chambers 28. Such textures may comprise any of a nearly infinite range of random or patterned arrangements of raised or depressed structures. FIG. 5A-FIG. 6C illustrate several examples of possible texture arrangements. FIG. 5A shows a series of substantially linear longitudinal channels 92 that may be formed on an outer surface of a delivery chamber. FIG. 5B shows a pattern of cross-hatched channels 94 that may be formed on an outer surface of a delivery chamber. FIG. 5C shows a plurality of cellular structures 96 that may be formed on an outer surface of a delivery chamber. FIG. 5D shows a pattern of wavy longitudinal channels 98 that may be formed on an outer surface of a delivery chamber.

In various embodiments, the expandable section may be fabricated in any size or size range for targeting an intended body lumen. In some cases, the expandable section may be sized to treat vascular anatomy. For example, the expandable section may be sized to have an un-expanded diameter (e.g., a distance between the seams 22, 24) of between about 2 mm and about 20 mm. In other embodiments, the expandable section may be sized to have an un-expanded diameter of between about 2 mm and about 12 mm. The expandable section may also be sized to have a length of between about 0.5 cm and about 100 cm or longer. In other embodiments, the expandable section may also be sized to have a length of between about 10 cm and about 15 cm.

In various embodiments, a proximal end of the catheter body 30 may be joined to a handle section configured to facilitate injecting an inflation medium through the inflation lumen 32 into the inflation chamber 26 and injecting one or more therapeutic agents through a delivery lumen 34 and into and through apertures in a delivery chamber 28. Many suitable handle structures are available.

Figure 8:
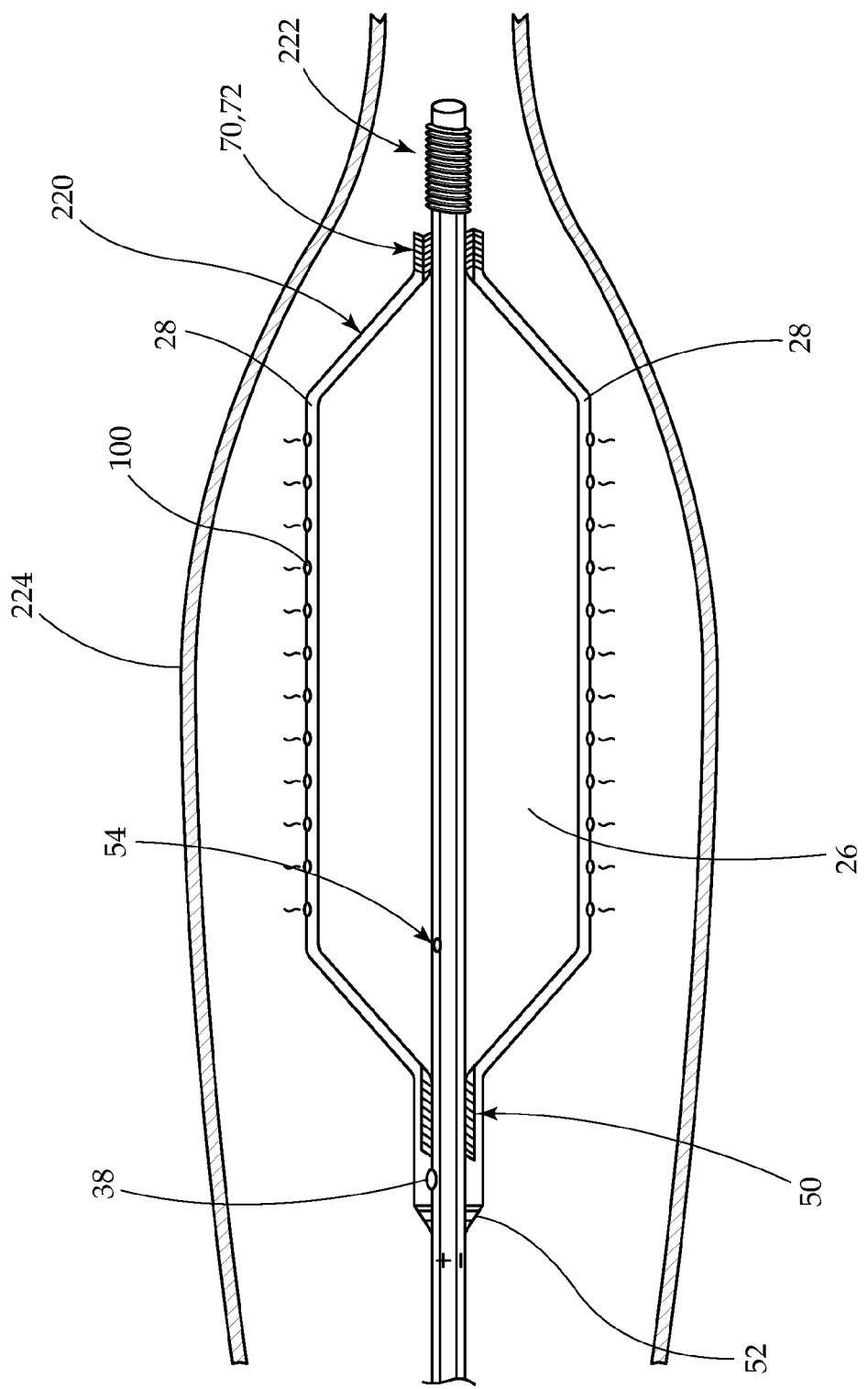
FIG. 8 is a longitudinal cross-sectional diagram of an example of an expandable multiple chamber therapeutic agent delivery device positioned in a body structure.

FIG. 8 illustrates another embodiment of a device 220 that may incorporate a heating element 222 for further sclerosing a body lumen wall 224. For example, the heating element may be used during a sclerosing treatment to heat a blood vessel wall distal to the expandable section in order to denature the collagen in the vessel wall and invoke a contraction or shrinkage of the vessel. This may provide benefits when treating a Greater Saphenous Vein, such as by causing the vein near the Saphenofemoral Junction to shrink or close before a targeted delivery of a therapeutic agent through the delivery chamber(s) 28. In some embodiments, such a procedure may be done under local or no anesthesia by operating the heating element 222 at a relatively low temperature range, such as in a range from 40° C. to 75° C. However, at higher temperatures the expandable section of the device could be used to introduce lidocaine or other local anesthetic prior to treatment.

Methods of Therapeutic Use

Figure 7:
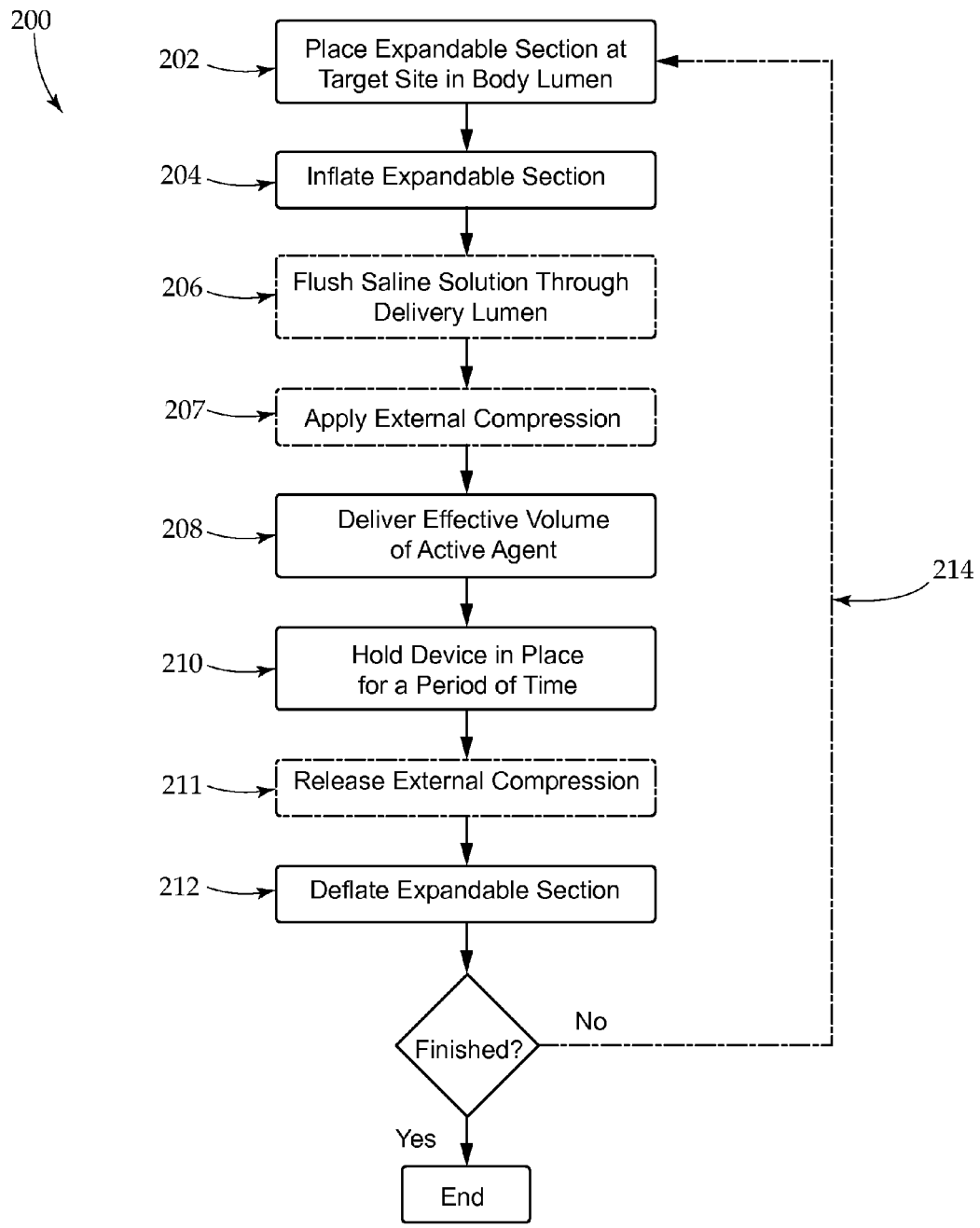
FIG. 7 is a diagram illustrating an example of a process for delivering a therapeutic agent to a targeted body structure using an expandable multiple chamber therapeutic agent delivery device.

FIG. 7 is a process flow chart illustrating an embodiment of a process 200 for using a multi-chamber expandable therapeutic agent delivery device having features such as those described above in order to treat a target site in a body lumen. An expandable device carried on the distal end of a catheter body may be percutaneously inserted into the body lumen to be treated and advanced until the device is positioned at a target location as indicated by block 202. In some embodiments, positioning of the expandable section may be performed while visualizing the target body structure using fluoroscopy, ultrasound (with or without a contrast agent) or other imaging modality. Once in position, the inflation chamber 26 of an expandable section may be inflated sufficiently to exclude blood or other liquid from the lumen and to contact the lumen wall as indicated in block 204. In some embodiments, a sufficient expansion of the expandable section may be detected based on a measured static fluid pressure of an incompressible inflation medium used to inflate the inflation chamber 26. For example, in some embodiments, determining that a saline inflation medium in the inflation lumen is at a pressure of about ~0.5 atmospheres (about 0.5066 bars).

In some embodiments, at the optional block 206, a volume of saline may be flushed through the delivery lumen 34 and through the delivery chambers 28 in order to wash a target area. In some embodiments, at the optional block 207, an external compression force may be applied to a body portion adjacent a treatment site.

An effective volume of an active agent may then be delivered as indicated at block 208. In some embodiments, as indicated by block 210, the device may be held in place at the target site for a dwell time period sufficient to allow the active agent to have a desired effect. For example, in some embodiments, the device may be held in place at a target site for about 1 minute. Alternatively, depending on the particular therapeutic objectives, a dwell time of 1 or 2 seconds up to 10 minutes or more. In other cases, a dwell time of 1-5 minutes may be suitable. If compression was applied at block 207, such pressure may be released at block 211 once a desired time has elapsed.

As indicated by block 212, after a sufficient period of time has elapsed the expandable section may be at least partially deflated, such as by briefly venting the inflation lumen, allowing a small volume of an inflation fluid to flow proximally from the inflation chamber through the inflation lumen. In some embodiments, if additional treatments at the same target site are desired, the expandable section may be twisted or rotated without axially re-positioning the device, and steps 204-210 may be repeated. In some cases, if the treatment is complete, the device may be substantially entirely deflated and removed. Alternatively, if additional target sections are to be treated, the expandable section may be only partially deflated, and the expandable section may be re-positioned to a new target site within the same lumen or another body lumen.

In some embodiments, re-positioning the expandable section may include twisting and/or axially moving the expandable section. In some embodiments, a second target at which a second therapeutic agent delivery step is to be performed may at least partially overlap the first target site, in some embodiments by 1 cm or more, or less in other embodiments. In some embodiments, first and second target sites may be contiguous but non-overlapping, or the target sites may be dis-contiguous. The steps of blocks 202-212 may optionally be repeated as indicated by the dashed line 214 to treat the new target section.

In some embodiments, re-positioning the expandable section may include removing the expandable section from the patient and re-inserting the expandable section into a new region or body lumen to be treated.

In some embodiments, external compression may be maintained or re-applied even after partially or completely deflating and/or removing the expandable member from the first target region. For example, in some embodiments, a treated limb or other body segment may be wrapped with a compression bandage for a period of time (e.g., 15 minutes, more or less) after delivering a therapeutic agent to one or more target sites. Any or all of the foregoing steps may be repeated as many times as needed.

Clinical Uses

Any of the various embodiments of expandable multi-chamber therapeutic agent delivery devices described above may be used to directly deliver one or more therapeutic agents to a target region within a body lumen, a body cavity or other body structure with an interior wall. Various treatments may include delivering therapeutic agents selected to achieve a desired therapeutic result such as to maintain lumen patency by preventing restenosis or by forming scar tissue in a lumen wall, causing occlusion or collapse of a target lumen, altering nerve or muscle function, causing targeted tissue modification or cell death, etc. This section provides some examples of therapeutic procedures and/or targeted body structures that may be treated by the delivery of one or more therapeutic agents. Specific examples of therapeutic agents that may be used are provided further below.

In some embodiments, portions of blood vessels with arterial plaque may be treated by delivering one or more anti-restenosis agents to a portion of a vessel wall.

In some embodiments, portions of a gastrointestinal tract in patients suffering from a condition such as gastroesophageal reflux disorder (GERD) or other disorders may be treated by delivering one or more therapeutic agent to a targeted section of an esophagus, stomach, intestine or colon.

In some embodiments, a device such as those described above may be used to deliver an effective quantity of a sclerosing agent to a vascular vessel such as a varicose saphenous vein or another varicose vein. In some embodiments, an effective quantity of a sclerosant may be a quantity sufficient to cause fibrotic occlusion of the target vessel.

Sclerotherapy can be used to treat blood vessels and vascular malformations in the body as well as other medical conditions and has been in use in one form or another for over 150 years. Sclerotherapy was first used in 1936 in a procedure in which a sterile solution was injected into the lumen of a vein for the purpose of producing irreversible, full-thickness mural denaturation.

In modern day utilization of sclerotherapy, new techniques have been devised including modifying the liquid sclerosing agent with air or CO2 to create foam used to improve the displacement of blood in the vessel in the attempt to improve full vessel wall contact and minimize the detrimental creation of endovascular thrombus. However, it is noted that significant harmful complications resulting from foamed sclerosants have been evidenced, including blood clotting throughout the vascular system where the foam has migrated, as well as bubble formation in the bloodstream leading to neural Transient Ischemic Attacks from bubbles reaching the neurovascular through patients with patent septal defects.

In some embodiments, a device such as those described above may be used to deliver an effective quantity of a sclerosing agent to other vascular structures including, but not limited, to: blood vessels such as perforating veins which connect the superficial veins to the deep veins in the leg, truncal superficial veins of the leg (e.g., great saphenous vein, short saphenous vein, and the like), superficial tributary veins of the leg, telangiectasia, internal spermatic veins (varicoceles), ovarian veins, gonadal veins, hemorrhoidal vessels, venous malformations, arteriovenousfistula networks, lumbar arteries, feeding vessels into the aorta to prevent abdominal aortic aneurysm (AAA) graft endoleaks, aortic aneurysm excluded lumens post AAA graft placement, arteriovenous malformations, neurovascular arteriovenous malformations, neurovascular aneurysm treatment, splenic artery trauma, and the like.

Effective sclerotherapy typically requires irreversibly altering substantially an entire section of a vascular or other body lumen wall including endothelial cells, tunica intima, tunica media, and tunica adventitia. If a sufficient irreversible alteration is achieved, mural repair and subsequent recanalization cannot occur and the vessel will be resorbed by the body.

Sclerotherapy is currently used for the treatment of various conditions including but not limited to: truncal varicose veins, tributary varicose veins, reticular veins, telangiectasia, spider veins and sometimes fine facial and hand veins. Treatment of these conditions may be performed by injecting sclerosing solution into the vessel to cause destruction of the vessel through vascular fibrosis and obliteration in response to irreversible endothelial cellular destruction and exposure of the underlying sub-endothelial cell layer. Destruction may occur when the liquid sclerosing solution is injected into the vessel. However, when injected, the sclerosing liquid typically mixes with the blood in the vessel and is diluted in unknown proportion. The results are uncertain and unpredictable. If the injected sclerosing agent is too weak, there may be no tissue damage at all. If the sclerosant is slightly stronger, the vessel may be damaged, but recanalization may occur and an incompetent pathway for retrograde blood flow may persist. Finally, if the injected sclerosant is too strong or powerful, the endothelium may be destroyed, but adjacent vessels that have not been targeted for treatment may also be damaged by the sclerosing agent.

Additionally, establishing an ideal strength of a sclerosant is complicated by the constant flow of blood through the vessel that is being treated. This flow simultaneously dilutes, and thereby weakens the sclerosant, while also transporting the sclerosant to other parts of the vascular system that have not been targeted for treatment.

Since the inception of sclerotherapy, it has been thought that the production of an intravascular thrombus was a prerequisite for vein sclerosis. In fact, intravascular thrombosis is an impediment to the complete resorption and disappearance of the vessel. Intravascular thrombus occurring after successful sclerotherapy develops in the presence of significant mural damage and is firmly adherent to the vein wall remnants. This thrombus is unlike thrombophlebitis which forms when residual blood mixing with the sclerosing solution creates intravascular thrombus that is not firmly attached to the vessel wall and is associated with incomplete mural disruption and unsuccessful sclerotherapy. The presence of a large intraluminal thrombus increases the likelihood of clinically apparent, symptomatic superficial thrombophlebitis. Consequently, this is one limitation of several of the current sclerotherapy techniques in existence today.

Another limitation of sclerosing treatments today is the concentration of the sclerosing agents in certain target blood vessels. For example, some regulatory limitations restrict the concentration of sclerosing agents to less than 3% concentration if the target vein is less than 4 mm in diameter. In such concentrations, the sclerosing agent may be rapidly diluted and therefore not sufficiently effective for treating the surrounding veins. Increasing the quantity and/or the concentration of the injected sclerosing agent to offset the dilution may introduce harmful quantities into the body.

These and other challenges in performing effective sclerotherapy may be overcome through the use of any of the various devices described above. Such devices may improve sclerotherapy procedures by simultaneously excluding blood from the target vessel while allowing for delivery of an effective quantity of sclerosing agent directly to the vessel wall. By delivering sclerosant directly to the vessel wall to be treated, a smaller volume of sclerosant may be delivered to the vessel, thereby improving safety and potentially expanding the scope of treatments that may be offered, such as by allowing for bilateral treatment (both legs) before reaching a maximum allowable sclerosant dosage. Providing such a device at a low cost may make such procedures available to a wider range of patients.

In some embodiments, such a device may be configured to treat a target vessel section while the device remains substantially stationary within the vessel. Vessel sections longer than the expandable section of the device may be treated by segmentally re-positioning the expandable section and applying an additional treatment. Such a mode of operation may eliminate the need to pull a device through a vessel as is required with other devices. Eliminating the need to pull the device at a constant rate while applying treatment may substantially simplify treatment, thereby improving outcomes. A device allowing for efficient sclerotherapy without necessarily requiring the application of energy (e.g., heat, laser, RF, etc.) may also eliminate or reduce the need for tumescent anesthesia.

Additional body structures to be treated by targeted delivery of one or more therapeutic agents using an expandable multi-chamber therapeutic agent delivery device may include lungs or airways, (e.g., in the treatment of emphysema or COPD), esophageal varices, fallopian tubes, vas deferens, nasal passages (e.g., in the treatment of treatment of sleep apnea, nasal valve insufficiency, etc.), chemotherapy treatment for Barrett's Esophagus or other cancers, hemorrhoids, varicoceles, pelvic congestion syndrome, sleep apnea, Abdominal Aortic Aneurysm treatment, neurovascular Aneurysm treatment, atherosclerotic plaque, renal artery denervation, permanent female contraception (i.e. fallopian tube occlusion), Deep Vein Thrombosis treatment, pelvic varices, or others.

In various other embodiments, any other body lumens, vessels, cavities, voids, organs or other structures may also be treated using a device such as those described above to deliver a therapeutic agent.

Therapeutic Agents

According to any of the foregoing therapies or others, an expandable multi-chamber therapeutic agent deliver device may be used to deliver one or more therapeutic agents to a target structure. Such therapeutic agents may generally include analgesics, anti-restenosis agents, sclerosants, chemotherapeutic agents, other pharmacological agents, hormone agents, or others. Specific examples of these and other therapeutic agents are provided below.

In some embodiments, one or more regions of a patient's vasculature may be treated by delivering an effective quantity of a non-sclerosing agent. For example, an artery with plaque may be treated with an anti-restenosis agent such as paclitaxel, Limus, Sirolimus, Heparin, and the like.

In some embodiments, other blood vessels may be treated by delivering a therapeutic agent including a blood thinner such as warfarin/coumadin, anticoagulants such as Heparin, Dalteparin sodium, Argatroban, Bivalirudin, Lepirudin, Heparin/Dextrose, Heparin Sodium, Aspirin (Ecotrin), Thrombin, Clopidogrel (Plavix).

In some embodiments, a therapeutic agent delivered using a device such as those described above may include platelet aggregation inhibitors such as Abciximab, which is a glycoprotein IIb/IIIa receptor inhibitor manufactured under the trade name ReoPro, and is a platelet aggregation inhibitor mainly used during and after coronary artery procedures such as angioplasty in order to prevent platelets from sticking together and causing thrombus (blood clot) formation within the coronary artery.

In some embodiments, a therapeutic agent delivered to a target body structure may include a pharmacologically inactive body neutral substance such as sterile saline solution.

In some embodiments a device such as those described above may be used to deliver a sclerosant. In such embodiments, the therapeutic agent may include sodium tetradecyl sulfate (Sotradecol®), polidocanol (Asclera®), echanolamineoleate (Ethamolin®), morrhuate (Scleromate®) or any other suitable sclerosing agent. In some embodiments, sodium tetradecyl sulfate may be used in a concentration of between about 0.5% and about 5% mass by volume (e.g., 0.5% may be 5 mg/ml). In some embodiments, polidocanol may be used in a concentration of between about 0.5% and about 5% mass by volume.

Sclerosants may include those conventionally employed in sclerotherapy to close veins. Detergent sclerosants work by a mechanism known as protein theft denaturation, in which an aggregation of detergent molecules forms a lipid bilayer in the form of a sheet, a cylinder, or a micelle, which then disrupts the cell surface membrane and removes proteins from the cell membrane surface. The loss of protein causes a delayed cell death. Unlike many other agents, the detergent sclerosants do not cause hemolysis, nor do they provoke direct intravascular coagulation.

Sodium morrhuate is a detergent sclerosant made up of a mixture of saturated and unsaturated fatty acids extracted from cod liver oil. It is a biological extract rather than a synthetic preparation, and the composition can vary from lot-to-lot, and a significant fraction of its fatty acids and alcohols are of chain lengths that probably do not contribute to its effectiveness as a sclerosant. It is unstable in solution, causes extensive cutaneous necrosis if extravasated, and has been responsible for many cases of anaphylaxis.

Ethanolamine oleate, a synthetic preparation of oleic acid and ethanolamine, has weak detergent properties because its attenuated hydrophobic chain lengths make it excessively soluble and decrease its ability to denature cell surface proteins. High concentrations of the drug are necessary for effective sclerosis, and its effectiveness in esophageal varices depends upon mural necrosis. Allergic reactions are uncommon, but there have been reports of pneumonitis, pleural effusions, and other pulmonary symptoms following the injection of ethanolamine oleate into esophageal varices. It has a high viscosity that makes injection difficult, a tendency to cause red cell hemolysis and hemoglobinuria, the occasional production of renal failure at high doses, the possibility of pulmonary complications, and a relative lack of strength compared with other available sclerosants.

Sodium tetradecyl sulfate is a synthetic long chain fatty acid that is sold for medical use as a solution of up to 3% concentration with 2% benzoyl alcohol used as a stabilant. It is effective as a venous sclerosing agent in concentrations from 0.1% to 3%, and has proven to be a reliable, safe and effective sclerosant. The principal clinical problems with the drug are a tendency to cause hyperpigmentation in up to 30% of patients, a significant incidence of epidermal necrosis upon extravasation, and occasional cases of anaphylaxis.

Polidocanol (hydroxy-polyethoxy-dodecane) is a synthetic long-chain fatty alcohol employed as a sclerosant. Polidocanol is painless upon injection. It does not produce necrosis if injected intradermally, and has been reported to have a very low incidence of allergic reactions. Occasional anaphylactic reactions have been reported. In some patients it may produce hyperpigmentation, although to a lesser extent than many other agents. Telangiectatic matting after sclerotherapy with polidocanol is as common as with any other agent. Scleremo, a compound of 72% chromated glycerin, is a polyalcohol that is a very weak sclerosant and is principally useful in the sclerosis of small vessels. Its principal advantage is that it rarely causes hyperpigmentation or telangiectatic matting, and that it very rarely causes extravasation necrosis. The main problems with scleremo are that it is hard to work with because it is extremely viscous, that it can be quite painful on injection, that the chromate moiety is highly allergic, and that it has occasionally been reported to cause ureteral colic and hematuria.

Strong solutions of hypertonic saline and other salt solutions are part of a class of solutions that are often referred to as osmotic sclerosants. These solutions have long been regarded as causing endothelial death by osmotic cellular dehydration. Hypertonic solutions of saline as agents for sclerotherapy can be prepared as 20% or 23.4% solutions. The principal advantage of saline is the fact that it is a naturally occurring bodily substance with no molecular toxicity. Because of dilutional effects, it is difficult to achieve adequate sclerosis of large vessels without exceeding a tolerable salt load. It can cause significant pain on injection, and significant cramping after a treatment session. If extravasated, it almost invariably causes significant necrosis. Because it causes immediate red blood cell hemolysis and rapidly disrupts vascular endothelial continuity, it is prone to cause marked hemosiderin staining that is not very cosmetically acceptable.

Sclerodex is a mixture of 25% dextrose and 10% sodium chloride, with a small quantity of phenethyl alcohol. A primarily hypertonic agent, its effects are similar to those of pure hypertonic saline, but the reduced salt load offers certain benefits. Like pure hypertonic saline, it is somewhat painful on injection, and epidermal necrosis continues to be the rule whenever extravasation occurs.

Polyiodinated iodine is a mixture of elemental iodine with sodium iodide, along with a small amount of benzyl alcohol. It is rapidly ionized and rapidly protein-bound when injected and most likely works by localized ionic disruption of cell surface proteins in situ. In vivo conversion of ionized iodine to iodide renders the solution ineffective as a sclerosant, thus localizing the sclerosing effects to the immediate area of injection. It has a high tendency to cause extravasation necrosis, its limited effectiveness at a distance from the injection site, and the risks of anaphylaxis and of renal toxicity that are associated with ionic iodinated solutions.

Other chemical sclerosants exist that act by a direct or indirect chemical toxicity to endothelial cells: by poisoning some aspect of cellular activity that is necessary for endothelial cell survival. Such agents are less useful to the extent that they also poison other bodily cells. They also lack another of the key attributes of a good sclerosant: they remain toxic to some degree even after extreme dilution, so that there is no real threshold below which injury will not occur.

In some embodiments a therapeutic agent delivered by a multi-chambered delivery device such as those described above may include one or more chemotherapy agents. For example, the therapeutic agent may include an Antracycline such as Doxorubicin (Adriamycin), Daunorubicin, Epirubicin, Idarubicin, orotheranti-tumor antibiotics such as Actinonycin-D, Bleomycin, Mitomycin-C. The therapeutic agent may also include an alkylating agent such as nitrogen mustards including mechloromethamine, chlorambucil, cyclophosphamide (Cytoxan), ifosfamide, melphalan; a nitrosourea such as streptozocin, carmustine (BNCU), lomustine; an alkyl sulfonatesuch as busulfan; a triazine such asdacarbazine (DTIC) ortemozolomide (Temodar); anethylenimine such asthiotepa, altretamine (hexamethylmelamine). The therapeutic agent may also include one or more platinum drugs such as cisplatin, carboplatin, oxalaplatin. The therapeutic agent may also include an Antimetabolite such as 5-fluorouracil (5-FU), 6-mercaptopurine (6-MP), Capecitabine (Xeloda®), Cladribine, Clofarabine, Cytarabine (Ara-C®); Floxuridine, Fludarabine, Gemcitabine (Gemzar®), Hydroxyurea, Methotrexate, Pemetrexed (Alimta®), Pentostatin, or Thioguanine. The therapeutic agent may also include a topoisomerase inhibitor such astopotecan, rinotecan, etoposide, teniposide, or mitoxantrone. The therapeutic agent may also include a mitotic inhibitor, including one or more taxanes such as paclitaxel (Taxol®) and docetaxel (Taxotere®), one or more epothilones such as ixabepilone (Ixempra®), one or more vinca alkaloids such as vinblastine (Velban®), vincristine (Oncovin®), and vinorelbine (Navelbine®), or estramustine (Emcyt®). The therapeutic agent may also include L-asparaginase, proteasome inhibitors such as bortezomib, or others.

A delivered therapeutic agent may also include one or more corticosteroids such as prednisone, methylprednisolone (Solumedrol®), and dexamethasone (Decadron®).

In some embodiments, a delivered therapeutic agent may include one or morehormone antagonist agents, such as for treatments including cancer, weight loss, menopause, acne treatment, etc. Such hormone antagonist agents may include but are not limited to: Aldosterone Antagonists, Androgen Antagonists, Antithyroid Agents, Calcimimetic Agents, Estrogen Receptor Modulators, Insulin Antagonists, Leukotriene Antagonists, Prostaglandin Antagonists.

In various embodiments, therapeutic agents delivered using an expandable multi-chamber therapeutic agent delivery device may include venoconstrictors/vasoconstrictors including, but are not limited to sodium, potassium, epinephrin, norepinephrine, phenylephrine, vasopressin, noradrenaline, and the like. Venoconstrictors may reduce the volume of a targeted vein or other lumen, such that there is less potential for blood flow which might decrease the concentration of another therapeutic agent. The targeted lumen may then be easier to treat. In some cases, sodium-potassium mixtures may be particularly suitable venoconstrictors, but any suitable venoconstrictor/vasoconstrictor-may be employed.

Any suitable physiologically active substance or excipient can be delivered to a targeted body structure using an expandable multi-chamber therapeutic agent delivery device such as those described above. Additional examples of such substances may include, but are not limited to, anti-inflammatory agents, anti-infective agents, anesthetics, pro-inflammatory agents, preservatives, cell proliferative agents, tretinoin, procoagulants, fillers, binders, surfactants, and the like.

Suitable anti-inflammatory agents include but are not limited to, for example, nonsteroidal anti-inflammatory drugs (NSAIDs) such aspirin, celecoxib, choline magnesium trisalicylate, diclofenacpotasium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasonedipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Anti-infective agents may include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidumcrystallinum; gatifloxacin; and sulfamethoxazole/trimethoprim.

Anesthetics may include, but are not limited to ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

Other substances that can be delivered using the devices and embodiments disclosed herein include various pharmacological agents, excipients, sclerosants, venoconstrictors, and other substances well known in the art of pharmaceutical formulations. Other substances include, but are not limited to, antiplatelet agents, anticoagulants, coagulants, ACE inhibitors, cytotoxic agents, ionic and nonionic surfactants (e.g., Pluronic™, Triton™), detergents (e.g., polyoxyl stearate, sodium lauryl sulfate), emulsifiers, demulsifiers, stabilizers, aqueous and oleaginous carriers (e.g., white petrolatum, isopropyl myristate, lanolin, lanolin alcohols, mineral oil, sorbitan monooleate, propylene glycol, cetylstearyl alcohol), solvents like Dimethyl Sulfoxide (DMSO), preservatives (e.g., methylparaben, propylparaben, benzyl alcohol, ethylene diaminetetraacetate salts), thickeners (e.g., pullulin, xanthan, polyvinylpyrrolidone, carboxymethylcellulose), plasticizers (e.g., glycerol, polyethylene glycol), antioxidants (e.g., vitamin E), buffering agents, glues including but not limited to biocompatible cyanoacrylates, and the like.

In some embodiments, therapeutic agents delivered using an expandable multi-chamber therapeutic agent delivery device may include biocompatible and bioabsorbable polymers such as those described, for example, in U.S. Pat. No. 6,423,085 to Murayama et al. and U.S. Pat. No. 6,676,971 to Goupil et al., the contents of which are hereby incorporated by reference in their entirety.

Such materials can include naturally occurring materials or materials derived from natural sources, or synthetic materials. Examples of biodegradable polymers which can be used include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyhydroxyalkanoates (PHAs), polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of the above materials, with or without added components.

Proteins such as collagen, fibrinogen, fibronectin, vitronectin, laminin, thrombin, and gelatin may also be employed.

Catgut, siliconized catgut, and chromic catgut are suitable for use in certain embodiments. Other naturally occurring materials include, but are not limited to, starches, cellulose, acetates, and thrombin. Selected natural materials can provoke a heightened inflammatory response, which can be desirable for facilitating the occlusion process.

2-Cyanoacrylic esters, more commonly referred to as cyanoacrylates, are suitable for use in certain embodiments for occluding a hollow anatomical structure. Cyanoacrylates are hard glass resins that exhibit excellent adhesion to high energy surfaces, such as tissue. The excellent adhesive properties of cyanoacrylate polymers arises from the electron-withdrawing characteristics of the groups adjacent to the polymerizable double bond, which accounts for both the extremely high reactivity or cure rate, and their polar nature, which enables the polymers to adhere tenaciously to many diverse substrates. The ability of cyanoacrylates to rapidly cure and bond to skin makes them particularly well suited for use as medical adhesives. Cyanoacrylate adhesives suitable for use as medical adhesives include octyl 2-cyanoacrylate marketed as DERMABOND™ topical skin adhesive by Ethicon, Inc., a Johnson & Johnson Company, of Somerville, N.J., and butyl cyanoacrylate marketed as VETBOND™ by World Precision Instruments, Inc. of Sarasota, Fla.

Cyanoacrylate adhesives for medical and veterinary use generally include the longer alkyl chain cyanoacrylates, including the butyl and octyl esters. Octyl cyanoacrylates are the most widely used cyanoacrylate adhesive for tissue sealing. When bonding to tissue, octyl cyanoacrylates are four times stronger and less toxic than butyl cyanoacrylate. However, butyl cyanoacrylate is sometimes preferred for sealing deeper lacerations because it breaks down more easily and can be absorbed by the tissue more quickly than octyl cyanoacrylate. Cyanoacrylate liquid monomers polymerize nearly instantaneously via an anionic mechanism when brought into contact with any weakly basic or alkali surface. Even the presence of a weakly basic substance such as moisture is adequate to initiate the curing reaction. The curing reaction proceeds until all available monomer has reacted or until it is terminated by an acidic species. The time of fixture for cyanoacrylate occurs within several seconds on strongly catalytic surfaces to several minutes on noncatalytic surfaces. Surface accelerators or additives enhancing the curing rate may be used to decrease the time of fixture on non-catalytic surfaces. The cyanoacrylate adhesive can be formulated into a bioerodable material by inclusion of a pore forming agent (e.g., an agent that is soluble in tissue fluids, and that dissolves to leave pores and fissures in the polymerized mass).

Other suitable adhesives can include epoxies, UV-activated adhesives, and heat-activated adhesives, as are known in the art. Suitable biocompatible materials for use as occluding devices or materials, or in the preparation of occluding devices, can include polysilicones, polyurethanes, and the like.

In certain embodiments, it can be preferred to employ a hydrogel as an occluding material. Hydrogels form a specific class of polymeric biomaterials, and are generally defined as two- or multi-component systems consisting of a three-dimensional network of polymer chains and water that fills the space between macromolecules. Depending on the properties of the polymer or polymers used, as well as on the nature and density of the network joints, such structures in an equilibrium can contain various amounts of water; typically in the swollen state the mass fraction of water in a hydrogel is much higher than the mass fraction of polymer. Two general classes of hydrogels can be defined: physical gels (pseudogels), where the chains are connected by electrostatic forces, hydrogen bonds, hydrophobic interactions or chain entanglements (such gels are non-permanent and usually they can be converted to polymer solutions by heating); and chemical (true, permanent) hydrogels with covalent bonds linking the chains.

The polymers used as hydrogels in the preferred embodiments preferably exhibit at least moderate hydrophilic character. In practice, to achieve high degrees of swelling, it is common to use synthetic polymers that are water-soluble when in non-crosslinked form. Typical simple materials employed as hydrogels include but are not limited to poly(ethylene oxide), poly(vinyl alcohol), polyvinylpyrrolidone, and poly(hydroxyethyl methacrylate). There are also natural polymers, such as polysaccharides, that can form hydrogels. Hydrogels commonly employed in soft contact lenses, wound dressings, drug-delivery systems, and the like, can be suitable for use in preferred embodiments. Hydrogels typically exhibit good biocompatibility in the contact with blood, body fluids, and tissues. Hydrogels can be employed that are capable of reacting to various environmental stimuli as temperature, pH, ionic strength, solute concentration, electric field, light, sound, and the like.

Hydrogels can be employed in any suitable shape or form, e.g., injectable liquid, or rod, plug, or other solid shape. A hydrogel in the form of a suitably sized swellable rod is particularly preferred for use in forming an occlusion in a hollow anatomical structure.

Alternatives and Variations

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A device for targeted delivery of a therapeutic agent, comprising:
   an elongated catheter body comprising an inflation lumen and at least one therapeutic agent delivery lumen;
   a first inner sheet and a second inner sheet, wherein the first inner sheet and the second inner sheet comprise a water impermeable material; and,
   wherein the first inner sheet comprises a first inner seam and the second inner sheet comprises a second inner seam, wherein the first inner sheet and the second inner sheet are sealed to one another at the first inner seam and the second inner seam, and wherein the first inner sheet and the second inner sheet defining an inflation chamber in a volume between the first and second inner sheets;
   a first outer sheet and a second outer sheet;
   wherein the first outer sheet comprises a first outer seam and the second outer sheet comprises a second outer seam, wherein the first outer sheet and the second outer sheet are sealed to one another at the first outer seam and the second outer seam, and wherein at least one of the outer seams incorporate at least one of the first inner seam and the second inner seam;
   a first delivery chamber comprising a volume between an outer surface of at least one of the first and second inner sheets and an inner surface of at least one of the first and second outer sheets;
   wherein the inner sheets are bonded to the elongated catheter body such that the inflation lumen is in fluid communication with the inflation chamber;
   wherein the outer sheets are bonded to the elongated catheter body such that the at least one therapeutic agent delivery lumen is joined in fluid communication with the first delivery chamber; and
   wherein the first delivery chamber is not in fluid communication with the inflation chamber.

2. The device for targeted delivery of a therapeutic agent of claim 1, further comprising a second delivery chamber that is not in fluid communication with the first delivery chamber.

3. The device for targeted delivery of a therapeutic agent of claim 2, wherein the first outer seam incorporates the first inner seam and wherein the second outer seam incorporates the second inner seam to define the second delivery chamber.

4. The device for targeted delivery of a therapeutic agent of claim 2, the at least one therapeutic agent delivery lumen of the elongated catheter body comprises a first therapeutic agent delivery lumen and a second therapeutic agent delivery lumen.

5. The device for targeted delivery of a therapeutic agent of claim 4, wherein the first therapeutic agent delivery lumen is in fluid communication with the first delivery chamber, and the second therapeutic agent delivery lumen is in fluid communication with the second delivery chamber.

6. The device for targeted delivery of a therapeutic agent of claim 4, wherein the first therapeutic agent delivery lumen and the second therapeutic agent delivery lumen are in respective fluid communication with the first delivery chamber and the second delivery chamber.

7. A method of using the device as in claim 2 to deliver the therapeutic agent to a targeted body structure in a patient, comprising the steps of:
determining a first target site;
positioning the first delivery chamber adjacent to the first target site within a body structure;
inflating an expandable section until the outer sheets contact an interior wall of the body structure;
delivering a volume of a first therapeutic agent through the delivery lumen such that the first therapeutic agent directly contacts the body structure interior wall;
holding the device in place for a period of time; and,
deflating, at least partially, the inflation lumen.

8. The method of claim 7, further comprising:
determining a second target site;
re-positioning the first delivery chamber at the second target site;
inflating the expandable section until the outer sheets contact an interior wall of the body structure;
delivering a volume of a second therapeutic agent through the delivery lumen such that the first therapeutic agent directly contacts the body structure interior wall;
holding the device in place for a period of time; and,
deflating, at least partially, the inflation lumen.

9. The method of claim 7, further comprising a step of flushing a volume of saline solution through the first delivery chamber prior to the delivering step.

10. The method of claim 7, further comprising delivering a second therapeutic agent through the second delivery chamber, the second therapeutic agent comprising a different composition than that of the first therapeutic agent.

11. The method of claim 7, further comprising a step of applying external compression to a surface of a body portion adjacent to the first target site.

12. The method of claim 11, further comprising steps of:
repeatedly applying external compression at the target site while the first therapeutic agent is delivered.

13. The device of claim 12, wherein the delivery of the first therapeutic agent is performed by direct wall contact of the body structure.

14. The method of claim 11, further comprising a step of applying external compression at the target site.

15. The method of claim 11, further comprising a step of repeatedly applying a treatment at numerous treatment sites along a vessel until completion of treatment.

16. The method of claim 7, further comprising a step of excluding blood flow from the target site within the body structure simultaneous to delivery of the first therapeutic agent.

17. The device of claim 7, wherein an excluding of blood flow and delivery of the first therapeutic agent are completed by the same device.

18. The device of claim 17, wherein the excluding of blood flow and delivery of the first therapeutic agent are completed by the delivery chamber and the expandable section.

19. The method of claim 7, further comprising a step of maintaining the device in a selected position on the target site for a dwell time sufficient to allow an active agent to have a desired effect.

20. The method of claim 19, wherein the dwell time exists in range from 1 second to 10 minutes and wherein pressure is released once a desired time has elapsed.

21. The method of claim 7, further comprising steps of:
venting the inflation lumen; and,
allowing a small volume of an inflation fluid to flow proximally from the inflation chamber through the inflation lumen until partial deflation is achieved.

22. The method of claim 7, further comprising steps of:
rotating the expandable section of the device, and,
maintaining the device at a same axially position when additional treatments at the same target site are desired.

23. The device for targeted delivery of a therapeutic agent of claim 1, wherein the elongated catheter body further comprises a second therapeutic agent delivery lumen.

24. The device for targeted delivery of a therapeutic agent of claim 1, wherein the first outer sheet and the second outer sheet comprise a porous material.

25. The device for targeted delivery of a therapeutic agent of claim 1, wherein the first outer sheet and the second outer sheet comprise a woven material.

26. The device for targeted delivery of a therapeutic agent of claim 1, wherein the first outer sheet and the second outer sheet comprise a set of through apertures.

27. The device for targeted delivery of a therapeutic agent of claim 1, wherein the outer sheets each comprise an outer surface and an inner surface and wherein the outer surfaces comprise a textured surface and wherein the inner surfaces comprise a textured surface.

28. The device for targeted delivery of a therapeutic agent of claim 1, wherein the inner sheets each comprise an outer surfaces, wherein the outer surfaces comprise a textured surface.

29. The device for targeted delivery of a therapeutic agent of claim 28, wherein the set of flow promoting structures is selected from the group consisting of rods, wires, tubes, beads, woven materials, textiles, strips and netting.

30. The device for targeted delivery of a therapeutic agent of claim 1, further comprising a set of flow promoting structures positioned at an interface between the inner sheets and the outer sheets.

31. The device for targeted delivery of a therapeutic agent of claim 1, wherein the catheter body comprises a first therapeutic agent delivery lumen opening and a proximal seal between at least one of the outer sheets and the catheter body, wherein the first therapeutic agent delivery lumen opening is located adjacent to the proximal seal.

32. The device for targeted delivery of a therapeutic agent of claim 1, wherein the catheter body comprises a first therapeutic agent delivery lumen opening and a distal seal between at least one of the outer sheets and the catheter body, wherein the first therapeutic agent delivery lumen opening is located adjacent to the distal seal.

33. The device for targeted delivery of a therapeutic agent of claim 1, wherein the catheter body comprises a first therapeutic agent delivery lumen opening adjacent a proximal seal between at least one of the outer sheets and the catheter body and a distal seal between at least one of the outer sheets and the catheter body.

34. The device of claim 1, further comprising a therapeutic agent delivery tube extending at least partially through the first delivery chamber.

* * * * *